United States Patent
Smith

(10) Patent No.: US 9,934,461 B2
(45) Date of Patent: Apr. 3, 2018

(54) DOSE COUNTER AND DISPENSING APPARATUS

(71) Applicant: CONSORT MEDICAL PLC, Hemel Hempstead (GB)

(72) Inventor: Matthew Smith, Norfolk (GB)

(73) Assignee: CONSORT MEDICAL PLC, Hemel Hempstead, Hertfordshire (GB)

( * ) Notice: Subject to any disclaimer, the term of this patent is extended or adjusted under 35 U.S.C. 154(b) by 0 days.

(21) Appl. No.: 15/115,091

(22) PCT Filed: Jan. 29, 2015

(86) PCT No.: PCT/GB2015/050205
§ 371 (c)(1),
(2) Date: Jul. 28, 2016

(87) PCT Pub. No.: WO2015/114337
PCT Pub. Date: Aug. 6, 2015

(65) Prior Publication Data
US 2017/0004395 A1    Jan. 5, 2017

(30) Foreign Application Priority Data
Jan. 31, 2014   (GB) .................................. 1401698.4

(51) Int. Cl.
*G06M 1/22* (2006.01)
*G06M 1/04* (2006.01)
(Continued)

(52) U.S. Cl.
CPC ............ *G06M 1/22* (2013.01); *A61M 15/009* (2013.01); *A61M 15/0073* (2014.02);
(Continued)

(58) Field of Classification Search
CPC . G06M 1/22; G06M 1/24; G06M 3/02; B65D 83/14; A61M 15/009; A61M 15/0073
See application file for complete search history.

(56) References Cited

U.S. PATENT DOCUMENTS

| | | | |
|---|---|---|---|
| 2,550,103 A | 4/1951 | White | |
| 2011/0283997 A1* | 11/2011 | Walsh | A61M 15/0065 128/200.23 |
| 2014/0053833 A1* | 2/2014 | Cline | A61M 15/0065 128/203.12 |

FOREIGN PATENT DOCUMENTS

| | | |
|---|---|---|
| EP | 1859829 A1 | 11/2007 |
| EP | 2514468 A2 | 10/2012 |
| WO | 2005/079727 A2 | 9/2005 |

OTHER PUBLICATIONS

International Preliminary Report on Patentability for PCT/GB2015/050205 dated Aug. 2, 2016. 7 pages.
(Continued)

*Primary Examiner* — Donnell Long
(74) *Attorney, Agent, or Firm* — Smith, Gambrell & Russell, LLP

(57) ABSTRACT

The present invention provides dose counter for displaying a count indication of the number or quantity of doses dispensed from or remaining in a container associated, in use, with the dose counter, comprising an indicator member comprising dose indicia and a priming indicator for prompting a user to carry out one or more priming actuations of the container. The priming indicator is initially arranged to at least partially overly the indicator member to thereby at least partially obscure viewing of the dose indicia of the indicator member until the one or more priming actuations of the container have been completed. The priming indicator is movable after the one or more priming actuations have been completed into a disposition where it no longer obscures (Continued)

viewing of the dose indicia of the indicator member. The invention also provides a dispensing apparatus comprising the dose counter.

35 Claims, 10 Drawing Sheets

(51) Int. Cl.
*G06M 1/24* (2006.01)
*G06M 3/02* (2006.01)
*A61M 15/00* (2006.01)
*B65D 83/14* (2006.01)

(52) U.S. Cl.
CPC ............... *B65D 83/14* (2013.01); *G06M 1/04* (2013.01); *G06M 1/24* (2013.01); *G06M 1/248* (2013.01); *G06M 3/02* (2013.01)

(56) References Cited

OTHER PUBLICATIONS

International Search Report for PCT/GB2015/050205, dated Apr. 22, 2015 in English Language.
Written Opinion of the International Searching Authority for PCT/GB2015/050205, dated Apr. 22, 2015 in English Language.

* cited by examiner

DOSE COUNTER AND DISPENSING APPARATUS

The present disclosure relates to a dose counter and a dispensing apparatus incorporating such a dose counter. In one example it relates to dose counters incorporated in a pressurised metered dose inhaler or a pump.

BACKGROUND

It has been recognised in the past that there is a benefit in providing accurate information to a user of dispensing apparatus, such as pressurised metered dose inhalers (pMDIs), concerning the quantity of doses delivered from, or remaining in, the dispensing apparatus. Without such information, there is a risk that a user may be unaware that the dispensing container of the dispensing apparatus is empty or close to empty. This is a particular problem where the dispensing apparatus is for use in delivering medicinal compounds for the treatment of chronic or acute symptoms, for example, as in the case of a pMDI used for treating conditions such as asthma.

A pMDI typically comprises a pressurised dispensing container that is received in an actuator housing. The actuator housing will comprise an outlet through which substance can be dispensed. The outlet will typically be adapted for oral, nasal or sub-lingual delivery of the substance. The pressurised dispensing container typically comprises a canister which defines a storage volume for the substance to be dispensed, wherein an open end of the canister is closed by means of a metering valve. The metering valve is designed to accurately and consistently dispense a predetermined volume of substance on each actuation of the pMDI. The substance to be dispensed may be one of a wide range of substances. Typically, the substance will include one or more active components (such as medicaments) and a propellant that is volatile at standard pressures and temperatures.

To prepare a pMDI (or other dispensing apparatus) for use, it may be necessary to prepare or "prime" the metering valve of the pMDI by carrying out one or more actuations of the pMDI (which are not administered to the user) before putting the pMDI to normal use. Such priming actuations are designed to ensure that the metering valve of the pMDI is properly charged with the substance to be dispensed—since a metering chamber of the metering valve may initially be wholly or partly empty immediately after assembly of the pMDI. Thus the priming actuations are carried out to ensure that a full dose is delivered on the first 'normal' actuation by the user where administration of the substance is desired.

It is preferred that the priming actuations are carried out by the user when they first receive the pMDI, for example from a doctor or pharmacy, so that the metering valve is not potentially left for a long time between priming and its first normal use. Thus, there is a need for the instructions for the priming of the pMDI to be clear to the user. It is also preferable for any dose counter, that is present in the pMDI, not to record the priming actuations as dispensed doses. Rather, it is preferred that the dose counter should indicate that the pMDI is 'full' or shows the first it its series of numerical or other indicia after the priming actuations are completed.

EP2514468 describes a dose counter for a pMDI which comprises a tape reel bearing dose indicia that is moved from a first shaft to a second shaft past a viewing window during use of the pMDI. Priming dots are provided at the start of the tape reel which are initially displayed to a user to prompt them to carry out three priming actuations wherein the tape reel then displays the start of the sequence of numerical count indicia. Each portion of the tape reel is only viewed once by the user as it transits past the viewing window.

However, the use of priming dots at the start of a tape reel as described in EP2514468 is not suitable for use with dose counters of the type having one or more rotatable indicator members, especially where one or more of the rotatable indicator members may need to complete more than one revolution during the life of the dispensing apparatus.

According to the present disclosure there is provided a dose counter for displaying a count indication of the number or quantity of doses dispensed from or remaining in a container associated, in use, with the dose counter,
the dose counter comprising:
an indicator member comprising dose indicia; and
a priming indicator for prompting a user to carry out one or more priming actuations of the container;
wherein the priming indicator is initially arranged to at least partially overlie the indicator member to thereby at least partially obscure viewing of the dose indicia of the indicator member until the one or more priming actuations of the container have been completed;
wherein the priming indicator is movable after the one or more priming actuations have been completed into a disposition where it no longer obscures viewing of the dose indicia of the indicator member.

Advantageously, by using a priming indicator that at least partially obscures viewing of the dose indicia of the indicator member until the one or more priming actuations of the container have been completed, a simple and clear means of instructing the user to prime the dispensing apparatus is achieved. The use of the priming indicator does not negatively impact the readability of the dose indicia after the priming actuations have been completed. In addition, by making use of a priming indictor that at least partially overlies the indicator member the priming indicator finds use with a wide range of dose counter arrangements, especially those including one or more rotatable indicator members.

The priming indicator may be movable into the disposition where it no longer obscures viewing of the dose indicia of the indicator member by movement of the indicator member itself. In such a case, a simpler construction of dose counter may be achieved as no separate means need be provided to provide a motive force for moving the priming indicator.

The priming indicator may be initially coupled to the indicator member to thereby be moved with the indicator member during the one or more priming actuations. Thus, the priming indicator and the indicator member may be arranged to move in-sync with one another during the one or more priming actuations. Advantageously, the mechanism of the dose counter provided to achieve movement of the indicator member (which may be any one of a number of possible mechanisms) may also be used to move the priming indicator—avoiding the need for any separate source of motive force.

In such a case, the priming indicator is preferably able to be decoupled from the indicator member after the one or more priming actuations have been completed. Thus, during the remainder of the life of the dispensing apparatus movement of the indicator member need not move the priming indicator.

There are a number of possible means for decoupling the priming indicator. One possibility is that the priming indicator is able to be decoupled from the indicator member by the action of gravity. This allows for a simple arrangement where, for example, the priming indicator drops out of its coupled configuration.

The indicator member may comprise a rotatable member. In one example the indicator member comprises an annular ring wherein the dose indicia may be arranged on an outer peripheral face of the annular ring.

The indicator member and the priming indicator may comprise co-operating formations for coupling the priming indicator to the indicator member.

There are a number of possible configurations of co-operating formations for coupling the priming indicator to the indicator member. One possibility is where the co-operating formations comprise one or more legs provided on the priming indicator and one or more apertures in the indicator member. The one or more apertures may, for example, comprise one or more notches or indentations in an edge of the indicator member. In such a case, coupling may be achieved when the one or more legs of the priming indicator are engaged in the one or more apertures and decoupling may be achieved when the one or more legs are allowed to disengage from the one or more apertures. Preferably, the dispensing apparatus would be provided to the user with the priming indicator initially coupled to the indicator member—in this example, therefore with the one or more legs initially engaged with the one or more apertures. The use of notches or indentations in the edge of the indicator member may have the advantage of allowing easier decoupling of the priming indicator since decoupling can be achieved with a greater degree of choice of the direction of movement of the priming indicator relative to the indicator member. For example, the one or more legs may be moved either perpendicularly or parallel to the plane of the indentation or notch.

The priming indicator may be movable after the one or more priming actuations have been completed into a disposition where it no longer overlies the indicator member. In this position the priming indicator may, for example, be parked for the remainder of the life of the dispensing apparatus.

In some examples, the indicator member may form a first indicator member of the dose counter and the dose counter may further comprise a second indicator member; the first and second indicator members acting in combination to display the count indication. The use of two (or more) indicator members in combination may be useful in a number of circumstances. In one example, the two indicator members can be used to display a greater number of dose indicia than would be possible on a single indicator member. In another example, the two indicator members could display different, for example associated, indicia—for example, with the first indicator member displaying a numerical count and the second indicator member displaying a colour indication.

In such a case, the first indicator member may, for example, be arranged to move on each actuation of the associated container and the second indicator member may be arranged to move after a predetermined number of incremental movements of the first indicator member. Such an arrangement may be used wherein the dose indicia of the first indicator member displays a 'units' numeral (or other suitable marking/colour/indicia) of the count indication and wherein the second indicator member comprises dose indicia which display a 'tens' numeral (or other suitable marking/colour/indicia) and, optionally additionally a 'hundreds' numeral (or other suitable marking/colour/indicia) of the count indication.

It may be advantageous for the first indicator member to comprise a plurality of sequentially arranged arrays of 'units' numerals, each array ranging from '9' to '0'. Thus one complete revolution of the first indicator member may be configured to increment the second indicator member a plurality of steps.

Where the dose counter comprises at least two indicator members, the priming indicator may be initially arranged to at least partially overlie the first indicator member and to at least partially overlie the second indicator member to thereby at least partially obscure viewing of the dose indicia of both the first and second indicator members. This helps to prevent any of the dose indicia being mistakenly read until the one or more priming actuations have been completed.

Where the dosage counter comprises first and second indicator members, the priming indicator may be initially coupled to the first indicator member to thereby be carried with the first indicator member and to be moved relative to the second indicator member during the one or more priming actuations. The priming indicator may be arranged to be decoupled from the first indicator member after the one or more priming actuations have been completed. Optionally, the priming indicator may be arranged to become coupled with the second indicator member on decoupling from the first indicator member. Optionally, after coupling of the priming indicator to the second indicator member, the priming indicator may be carried with the second indictor member during subsequent actuations of the associated container. In such a case, it is preferred that the second indicator member is configured to complete less than a complete revolution (in the case of the indicator members being rotatable indicator members) during the lifetime of the dispensing apparatus so as to prevent the priming indicator returning into a position where it again obscures viewing of the dose indicia.

The first indicator member and the second indicator member may both comprise a rotatable member. The first indicator member and the second indicator member may each comprise an annular ring having dose indicia arranged on an outer peripheral face of the annular ring. The first indicator member, the second indicator member and the priming indicator may comprise co-operating formations for coupling the priming indicator initially to the first indicator member and subsequently to the second indicator member. As described above, the co-operating formations may, by way of example, comprise one or more legs provided on the priming indicator and one or more apertures in the first and second indicator members. The one or more apertures may comprise one or more notches or indentations in an edge of the first and/or second indicator members.

As in the above example, the priming indicator may be movable after the one or more priming actuations have been completed into a disposition where it no longer overlies the first indicator member.

According to the present disclosure the priming indicator may be a separate component from the indicator member. For example, the priming indicator may be a relatively small shutter-like component. The priming indicator may be shaped to conform generally to the shape of the first and/or second indicator member. For example, where the indicator member(s) are annular rings the priming indicator may comprise a body that is generally curved to match the curvature of the annular rings.

The priming indicator may comprise priming indicia suitable for viewing in place of the dose indicia of the indicator member until the one or more priming actuations of the container have been completed.

The present disclosure also provides a dispensing apparatus comprising a dose counter as described above.

The dispensing apparatus may further comprise a container containing a quantity of substance to be dispensed.

The dispensing apparatus may comprise a viewing window for viewing the count indication of the dose counter, wherein the priming indicator is initially arranged at least partially inbetween the indicator member and the viewing window to thereby at least partially obscure viewing of the dose indicia of the indicator member until the one or more priming actuations of the container have been completed;

wherein the priming indicator is movable after the one or more priming actuations have been completed into a disposition where it is no longer inbetween the viewing window and the indicator member.

In one example, the dispensing apparatus is a pressurised metered dose inhaler (pMDI). Another example of a use of a suitable dispensing apparatus is a pump, for example a nasal, oral or sub-lingual pump device.

The dose indicia of the indicator member(s) may be of any suitable type for conveying the necessary information to the user. Examples include numbers, letter, colours and pictograms. Such indicia may be used in combination if desired. For example, number indicia may be used as the main indicia (for example counting down from '200' to '000' doses remaining) combined with a change of colour indicia as the empty point approaches (for example the 'tens' or 'hundreds' indicator member may be provided with a red zone at or near the empty point).

The priming indicia of the priming indicator may be of any suitable type for conveying the necessary information to the user. Examples include dots, numbers, colours or pictograms. Preferably a different style of indicia is chosen for the priming indicia compared to the dose indicia.

The dispensing apparatus may be a pharmaceutical dispensing apparatus, such as, for example, a pulmonary, nasal, or sub-lingual delivery device. A preferred use of the dispensing apparatus is as a pressurised metered dose inhaler device for delivering a pharmaceutical in an aerosol form. Another use of the dispensing apparatus is as a pump device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, ipratropium bromide and salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and di-methyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

Rigid components of the dispensing apparatus may be formed from, for example, from polyester, nylon, acetal or similar.

BRIEF DESCRIPTION OF THE DRAWINGS

In order that the disclosure may be fully disclosed, an embodiment will now be described, by way of example, with reference to the accompanying drawings, in which:—

DETAILED DESCRIPTION

For the purposes of illustrating the dose counter and dispensing apparatus of the present disclosure they will be described with reference to the field of application of pressurised metered dose inhalers (pMDIs), an example of which is described in detail in the applicant's European patent publication EP 1 859 829. The contents of EP 1 859 829 are hereby incorporated by reference. However, it should be understood that the present disclosure is not limited to a dispensing apparatus of the specific design described below and in EP 1 859 829 but finds application with other dispensing apparatus, for example pump devices.

FIGS. 1 to 9 show a pMDI as described in EP 1 859 829 and are provided and described herein for the better understanding of the example of the present disclosure that will be described in detail further below.

Figure 1:
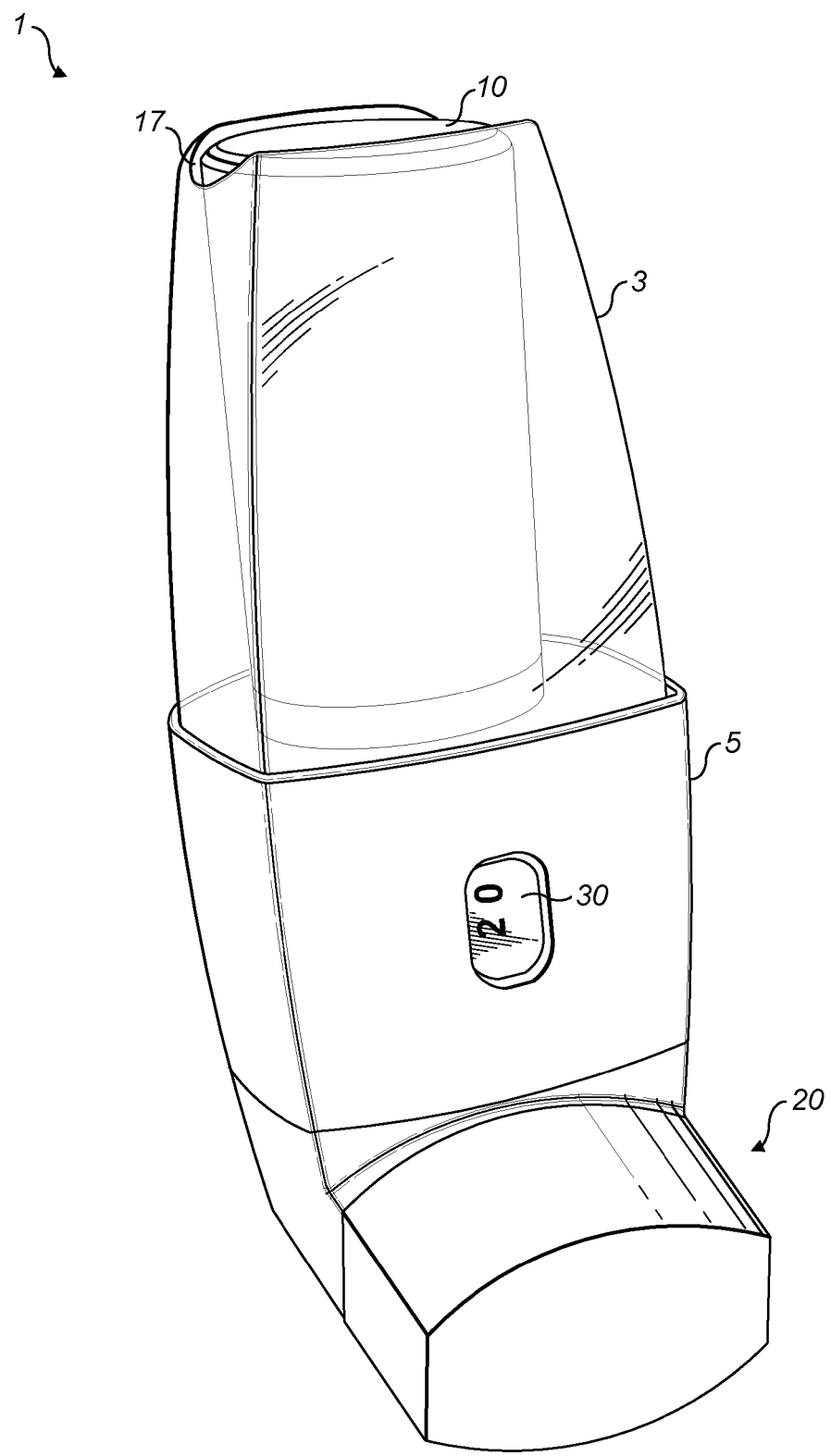
FIG. 1 is a perspective view of a dispensing apparatus as described in EP 1 859 829.
Figure 2:
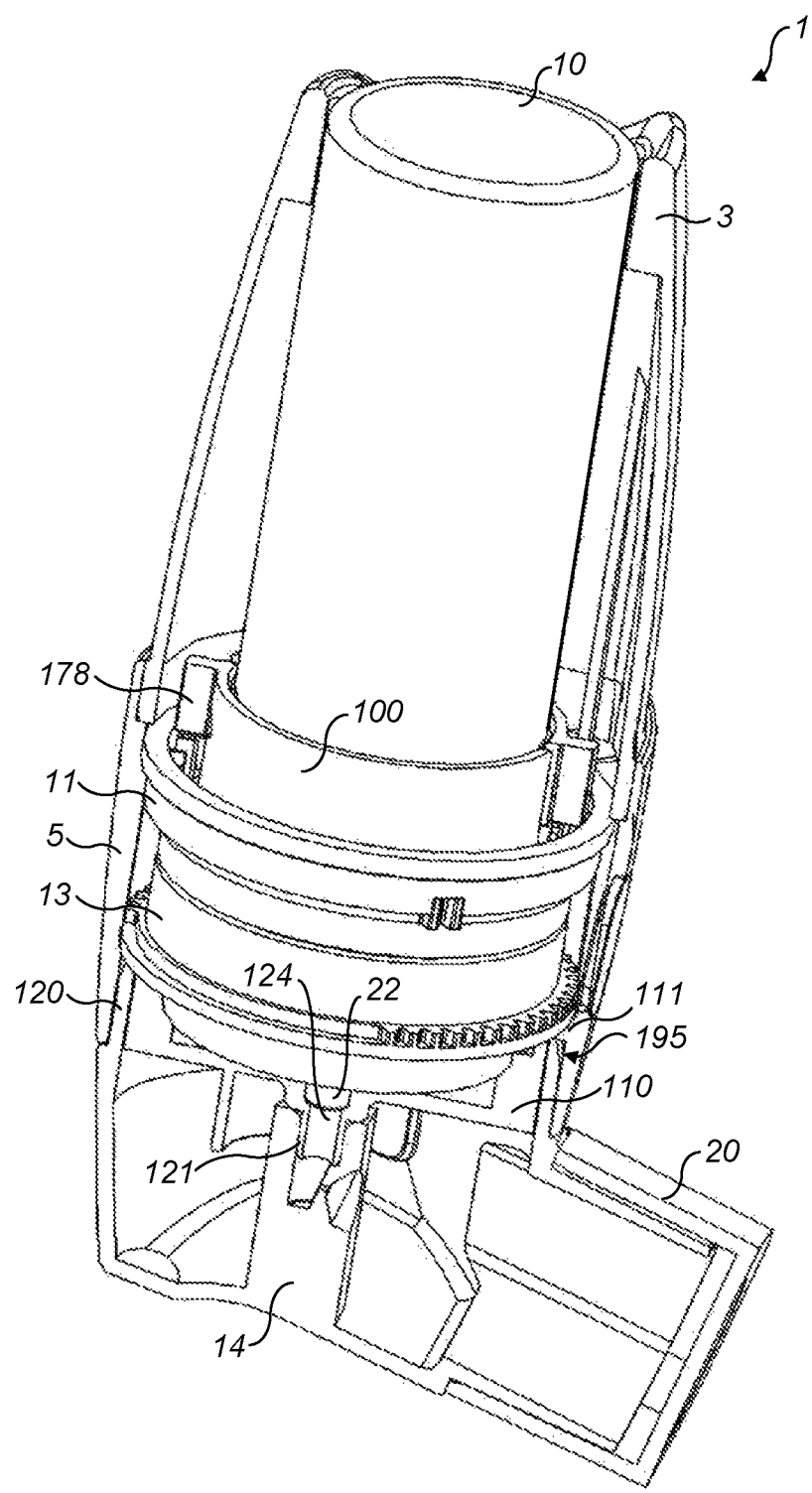
FIG. 2 is a cross-sectional view of the dispensing apparatus of FIG. 1.
Figure 8:
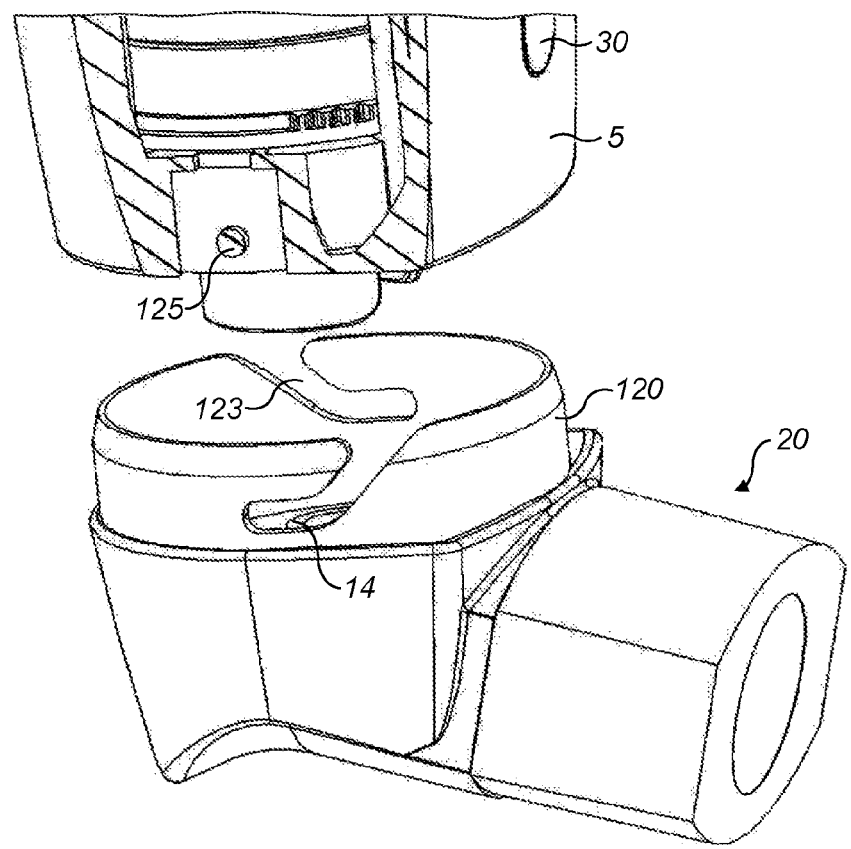
FIG. 8 is a perspective view of the dispensing apparatus of FIG. 1 with the mouthpiece detached and some parts shown in cross-section.
Figure 9:
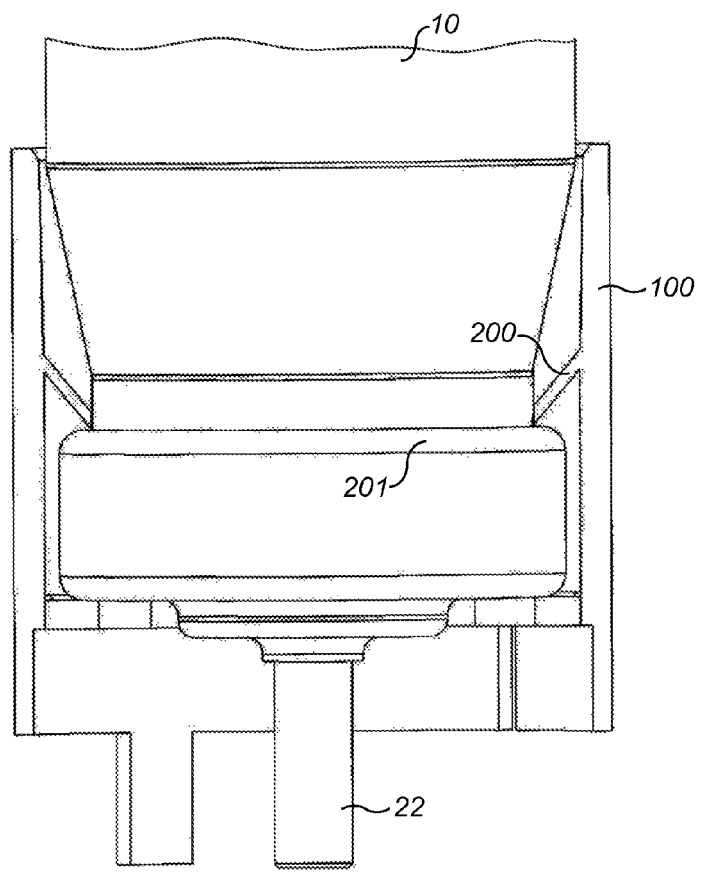
FIG. 9 is a schematic view of part of the apparatus of FIG. 1 with some parts omitted for clarity.

The dispensing apparatus, in the form of a pMDI, shown in FIG. 1, is indicated generally at 1, and has an upper body 3, a lower body 5 and a detachable mouthpiece 20 shown in FIG. 8. A dust cap may be used to cover the mouthpiece 20 when the apparatus is not in use. As shown in FIG. 2, the pMDI 1 also incorporates a dose counter having first and second number rings 11, 13, a cog 12 and a sleeve 100. The pMDI 1 holds a pressurised dispensing container 10.

The lower body 5 is open at its upper end. The lower body 5 houses the cog 12 and the first and second number rings 11, 13. As shown in more detail in FIG. 3, the number rings 11, 13 rest upon internal projections 111 of the main body 5. Such internal projections 111 provide up facing surfaces upon which the second number ring 13 may rest and rotate, during use. The first number ring 11 rests and rotates, during use, on top of the second number ring 13. The cog 12 is rotatably mounted within the main body 5 on a cylindrical portion 112 and interacts with both first and second number rings 11, 13. As can be seen, the axis of rotation of the cog 12 is offset from the axes of the numbered rings 11, 13 but parallel thereto so that the cog 12 can interact with both number rings 11, 13 which are housed in the substantially cylindrical part of the lower body 5 without impeding axial movement of the container 10. The lower body 5 is provided at a lower end thereof with an axial protrusion 121 integral with the lower body 5. The axial protrusion 121 comprises a hollow elongate portion into which the valve stem 22 of the container 10 can be received as a relatively tight interference fit. The hollow portion is provided with a narrowed constriction against which the valve stem 22 can abut when the dispensing apparatus is actuated. The hollow portion forms a conduit 124 that is in fluid communication with the outlet of the valve stem of the pressurised dispensing container 10 when the container is inserted into the apparatus. The axial protrusion 121 protrudes from the lower end of the lower body 5 as shown in FIG. 2. The axial protrusion 121 provides protection for the valve stem when the mouthpiece 20 has been removed and also directs dispensed product into the removable mouthpiece 20.

The lower body 5 and upper body 3 are connectable together using co-operating formations which are push-fit together as shown in FIG. 2.

The detachable mouthpiece 20 is attached to the main body 5 by means of a bayonet fitting. As shown in FIGS. 2 and 8 the mouthpiece 20 is provided with an upstanding rim 120 in which are formed two opposed recesses 123 of roughly an L-shape configuration. The main body 5 comprises a circumferential recess 195 which receives the rim 120 when the two pieces are coupled together. At opposed points of the circumferential recess 195 the lower body 5 is provided with retaining lugs 125 which pass along the recesses 123 of the mouthpiece. Thus the mouthpiece may be coupled to the lower body 5 by locating the lugs 125 relative to the upper end of the recesses and then twisting the lower body 5 relative to the mouthpiece 20 whilst applying a compressive axial force to the two components. This results in the lugs 125 riding along the recesses resulting in the two components being firmly connected. The mouthpiece 20 is also provided with a spray block 14 for receipt of the axial protrusion 121. The spray block 14 comprises a conduit having an upper end which receives the axial protrusion 121 and a lower end which comprises a spray outlet directed towards the outlet of the mouthpiece 20. The spray outlet may be provided with a suitably dimensioned orifice or spray pattern block as known in the art to produce an atomised spray of product on dispensation.

Figure 7:
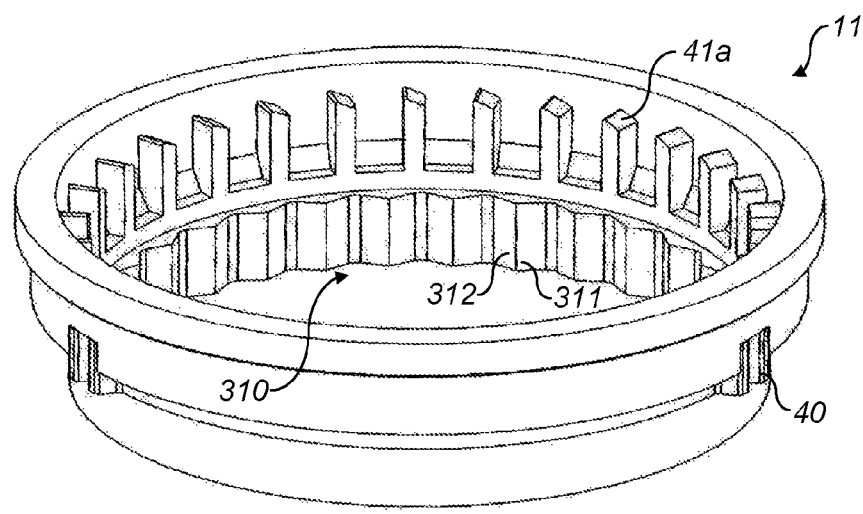
FIG. 7 is a perspective view of a first number ring having two different diameter portions, forming part of the dispensing apparatus of FIG. 1.

The first number ring 11 is provided with an upper row of angled abutment surfaces 41*a* located on a larger diameter portion of that number ring as shown in FIG. 7. A lower set of angled abutment surfaces are formed on a smaller diameter portion of the ring in the form of a series of inwardly directed projections 310 having a triangular cross-section when viewed from above. The projections 310 are arranged around the circumference of the lower portion of the ring 11 so as to form a series of interspersed peaks and troughs. Each projection 310 comprises two faces 311, 312 on either side of the peak. Preferably, the faces 311, 312 are arranged symmetrically about the peak. The faces 311 and 312 form angled abutment surfaces which engage the outward projection 304 of the tension arm 300 in use as will be described below.

The first number ring 11 comprises at least one notch 40 positioned on the outer edge thereof. The first number ring 11 is also provided with a set of numbering (not shown in FIGS. 1 to 9) from 0 to 9 for each notch 40, so that after each ninth actuation of the pMDI 1, a notch 40 is in position to interact with the cog 12. In one embodiment, the first number ring 11 will have three notches 40 and, so, will have three sets of numbering from 0 to 9 around its circumference.

Figure 4:
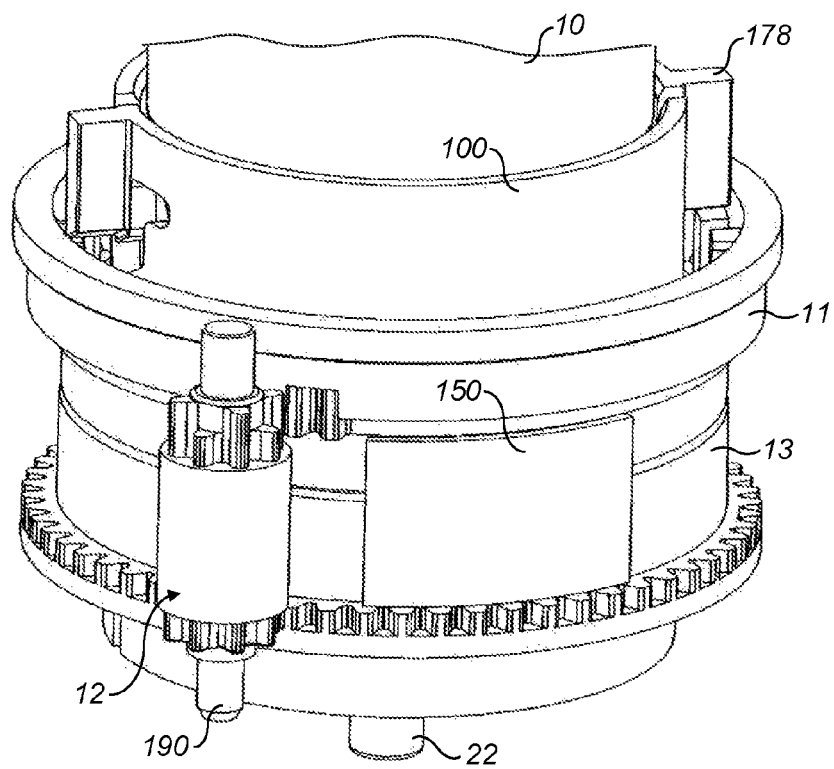
FIG. 4 is a perspective view of first and second number rings and a cog forming part of the dispensing apparatus of FIG. 1.

The second number ring 13 comprises a set of teeth 500 and may be provided with an extended portion 150, as shown in FIG. 4, which is positioned to enable covering of the markings on the first number ring 11 when the pressurised dispensing container 10 located in the pMDI is empty. Advantageously, the extended portion 150 provides a clear indication to a user that the pMDI has provided its full-quota of dispensations.

Figure 3:
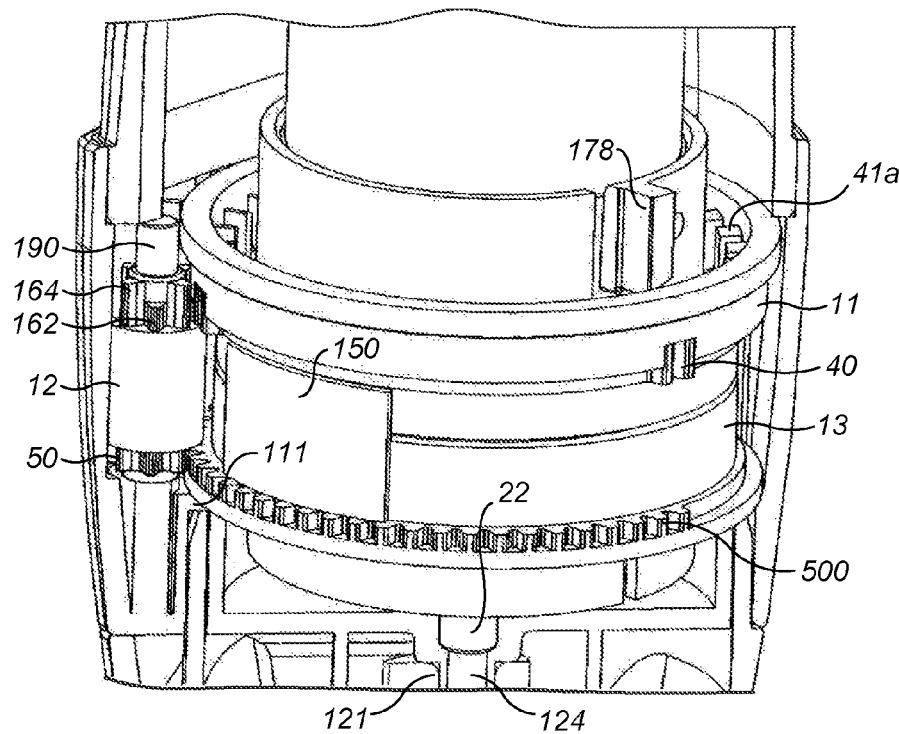
FIG. 3 is a perspective view of various internal features of the dispensing apparatus of FIG. 1.
Figures 5, 6:
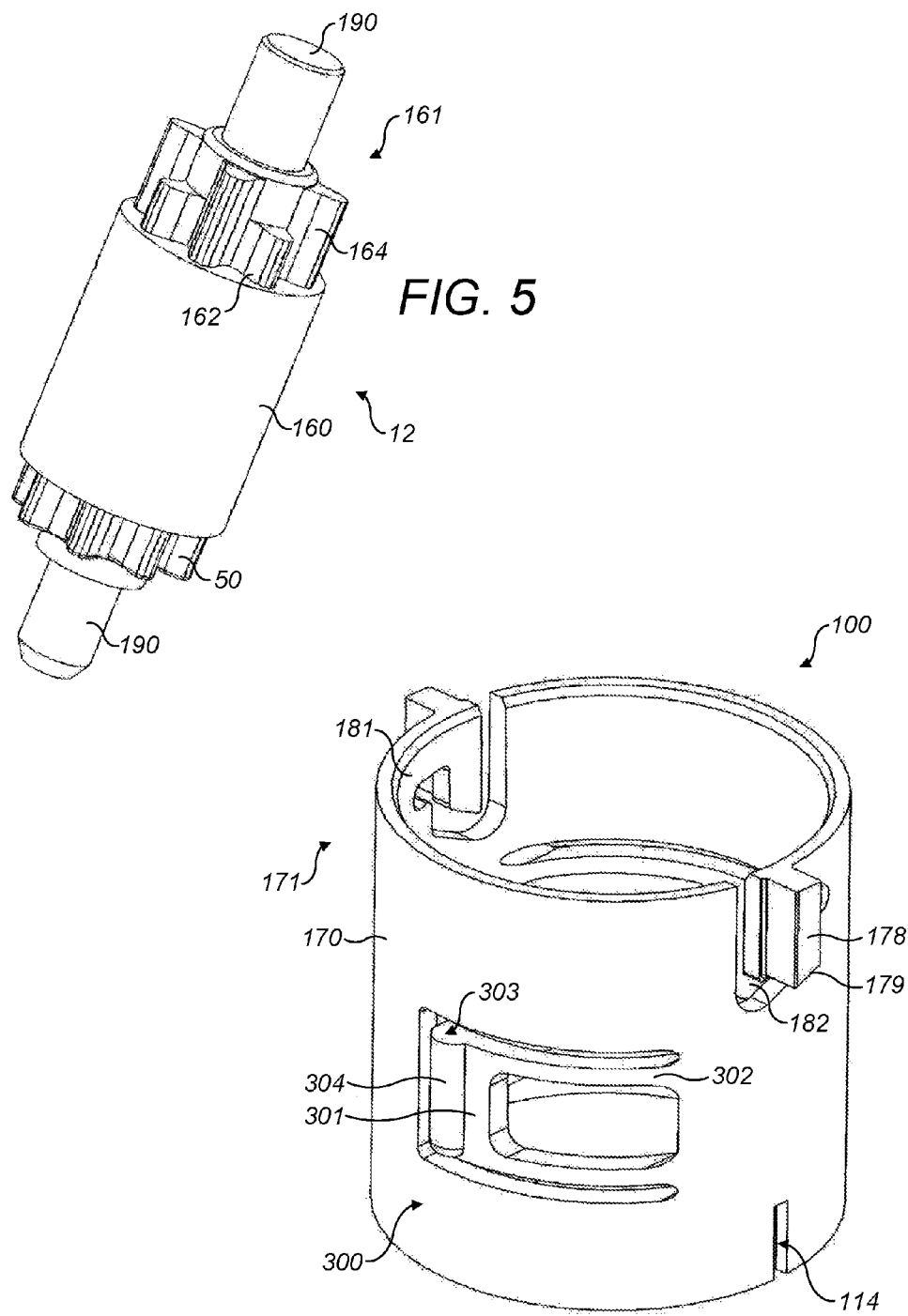
FIG. 5 is a perspective view of the cog forming part of the dispensing apparatus of FIG. 1.
FIG. 6 is a perspective view of a sleeve forming part of the dispensing apparatus of FIG. 1.

The cog 12, as shown in FIG. 5 in particular, is provided with one or more teeth separated by a non-toothed, cylindrical, spacer 160. A first end 161 of the cog 12 includes four teeth 162 of reduced height and four teeth 164 of full height which in use interact with the first number ring 11. The full height teeth 164 extend from the spacer 160 to the distal face of the first end 161 of the cog 12. The teeth 50 at a second end of the cog 12 are all full height and these teeth in use interact with the second number ring 13. The four teeth 162 having reduced height are, typically, half the height of the full height teeth 164. Most preferably, the reduced height teeth 162 and full height teeth 164 are arranged alternately around the circumference of the cog 12. The cog 12 is provided with upper and lower axial projections 190 which allow the cog 12 to be rotationally mounted in recesses formed in the lower body 5 as shown in FIG. 3.

As shown in FIGS. 2 and 6, the sleeve 100 comprises an open-ended cylinder 170 having an upper end 171 which can receive the container 10 to be located in the dispensing apparatus 1 and a lower end 172 which has a reduced diameter opening 173 through which the valve stem 22 of the pressurised dispensing container 10, located within the sleeve 100 may protrude from but through which the body of the container 10 cannot pass. The sleeve 100 is provided with two sets of formations on its exterior surface. The sets of formations are arranged diametrically opposite one another (only one set of formations is shown in FIG. 6). Each set of formations comprises first, second and third formations. The first formation is provided at the lower end 172 in the form of notches 114. The second formation is provided above the notches 114 in the form of a tension arm 300. The tension arm 300 comprises a cantilevered portion 301 which is fixed to the sleeve 100 at a hinge point 302. Preferably, the tension arm 300 is provided in a single moulding as part of the sleeve 100 in which case the hinge point 302 marks the junction between the body of the sleeve 100 and the start of the cantilevered portion 301 of the tension arm 300. A distal end 303 of the tension arm 300 is provided with an outwardly directed projection 304. It can be seen from FIG. 6 that the cantilevered tension arm 300 is able to accommodate flexure in a direction perpendicular to flexure of the cantilevered projection 178. That is, the outwardly directed projections 304 of the tension arm 300 can flex substantially radially inwards when pressure is applied to the projections in a radially inward direction. It will be appreciated that the shape of the container 10 must accommodate inward flexure of the tension arms 300. It is therefore preferable that the position of the tension arms 300 be located to coincide with a neck of the container 10 where it narrows to meet a ferrule of the metering valve, thereby forming an undercut. Alternatively, the walls of the container 10 may have formed in them depressions to accommodate inward flexure of the tensions arms 300. The third formation is provided at the upper end 171 in the form of a cantilevered projection 178. The cantilevered projection 178 comprises an elongated portion 180 having an angled abutment surface 179 on its lower, distal end. The elongated portion 180 of the cantilevered projection 178 is axially aligned with the projection 175. The elongated portion 180 is joined to the cylindrical body of the sleeve 100 at a hinge point 181. A void space 182 is formed around the elongated portion 180 to accommodate movement of the cantilevered projection 179 in use as will be described below.

The lower body 5 is provided with a clear portion 30, or one or more apertures 30, forming a viewing window through which portions provided with markings of the first and second number rings 11, 13 are visible. The upper body 3 is transparent to allow a user to easily see the type of container 10 located in the apparatus 1.

In use, the internal components of the dose counter, such as the cog 5, the sleeve 100 and the number rings 11, 13 can be loaded into position within the pMDI 1 by separating the upper body 3 from the lower body 5. The cog, number rings and sleeve 100 can be inserted into the opening of the lower body 5. The internal projections 110 of the lower body 5 are received slidingly in the notches 114 of the sleeve 100 with the effect that the sleeve 100 is fixed rotationally relative to the lower body 5. The sleeve 100 is arranged to pass through the central holes/apertures of the number rings 11, 13. The upper body 3 is then attached to the lower body 5.

The pressurised dispensing container 10 can now be passed through the hole in the upper body 3 to be received in the sleeve 100. The valve stem 22 of the pressurised dispensing container 10 is received in the opening of the conduit 124 of the axial protrusion 121 as a relatively tight interference push-fit. When loaded, the first and second number rings 11, 13 are located around the container 10 as shown in FIG. 3.

In the inserted position the upper end of the container 10 protrudes upwardly through the hole in the upper body 3 as shown in FIG. 1. Preferably, the container 10 only protrudes slightly above the level of the upper body 3. In the illustrated embodiment scallops 17 are provided in the upper edge of the upper body 3 and the container 10 protrudes above the level of the scallops but does not protrude above the highest part of the upper edge. The depth of the scallops 17 allows a user to depress the container 10 sufficiently to actuate the container's valve but reduces the area of the container 10 that can be gripped by the fingers of anyone attempting to remove the container 10 from the apparatus 1. Thus the amount of pulling force that can be applied to the container 10 is not enough to overcome the friction produced by the interference fit between the valve stem 22 and the conduit 124. Also, the fact that the container 10 does not protrude above the highest part of the upper edge helps to prevent accidental actuation of the apparatus when carried in the pocket.

The pMDI 1 is actuated by depression of the pressurised dispensing container 10 which protrudes above the scallops 17 of the upper body 3. Depression of the container 10 causes the container 10 and sleeve 100 to move axially within the main body 5 to actuate the container 10. Actuation causes an amount of product to be dispensed from the container 10 by an opposite reaction force from the constriction in the axial protrusion 121 acting on the valve stem 22, which is inwardly retracted relative to the remainder of the metering valve such that an amount of product is dispensed from the valve stem 22 through the conduit 124 and the valve stem receiving block 14, from where it is dispensed as an aerosol through the mouthpiece 20 and inhaled by a user inhaling on the mouthpiece 20. Release of the container 10 causes the container to return to its starting position, owing to the internal spring bias of the metering valve, ready for subsequent dispensing.

Each actuation of the pMDI 1 causes the first number ring 11 to rotate a partial increment during the downstroke of the pressurised dispensing container 10 owing to engagement of the angled abutment surface 179 of the cantilevered projection 178 with the angled abutment surfaces 41a the first number ring 11. This partial rotation of the first number ring 11 causes each outwardly directed projection 304 of each tension arm 300 to ride up an angled face 311 of respective protrusions 310. This movement is accommodated by the tension arms 310 as they flex radially inwards. The relative location of the angled abutment surfaces 41a and the projections 310 is such that when the downstroke of the sleeve 100 is completed the outwardly directed projections 304 of the tension arms 300 have ridden up the angled abutment surfaces 311 and over the peak of the projections 310 such that the outwardly directed projections 304 lie in contact with the angled abutment surfaces 312 of the projections 310. Thus, when the pressurised dispensing container 10 is released, and the sleeve 100 consequently moves back on its up stroke, the completion of the incremental rotation of the first number ring 11 is achieved by the biasing force of the outwardly directed projections 304 of the tension arms 300 on the angled abutment surfaces 312 as the tension arms 300 try to return to their unstressed position. This biasing force completes the rotation of the first number ring 11 such that the outwardly directed projections 304 of the tension arms 300 lie in the neighbouring trough between the projections 310 after one actuation. Consequently, the cantilevered projection 178 and the tension arm 300 (or the pairs of these features where present) act as first and second indexing members which together act to index the first number ring 11.

The first number ring 11 acts as the 'units' ring of the dose counter as it is moved on each actuation of the pMDI 1. The dose indicia on the first number ring 11 may comprise a plurality of sequentially arranged arrays of 'units' numerals, each array ranging from '9' to '0'. The first number ring 11 is intended to rotate fully a plurality of times during the life of the pMDI 1.

Every ten actuations of the pMDI 1 causes one of the notches 40 to pass the cog 12, the effect of this being that one of the full height teeth 164 of the upper row of teeth is caught in the notch 40 as it rotates, this rotation causing a corresponding rotation of the cog 12 in an opposite sense. As a consequence, the second number ring 13 is caused to rotate in the same sense as the first number ring 11 by interaction of the teeth 50 on the bottom of the cog 12 and the teeth 500 of the second number ring 13.

The second number ring 13 acts as the 'tens' or 'tens and hundreds' ring of the dose counter as it is moved after every ten actuations of the pMDI 1. The dose indicia on the second number ring 13 may comprise numerals donating the 'tens' and 'hundreds' numerals of the dose count. For example the numbering may range from to '20, 19, 18 . . . ' to ' . . . 3, 2, 1, zero/blank' to enable the dose counter to display counts ranging from '200' to zero. The second number ring 13 is intended only to rotate up to one revolution during the life of the pMDI 1.

FIGS. 10 to 17 illustrate an example of a dispensing apparatus according to the present disclosure, again in the exemplar form of a pMDI 1, which incorporates a dose counter, also according to the present disclosure. In describing the pMDI 1 and dose counter only those features which differ from the arrangement described above and shown in FIGS. 1 to 9 will be described in detail. In other respects, the features are as described above. In addition, the following description of the pMDI 1 and dose counter are provided by way of example only and it should be understood that the dose counter of the present disclosure is not limited to use with the pMDI 1 shown in FIGS. 1 to 9 but is only described incorporated in such a dispensing apparatus for the better understanding of the disclosure.

Figure 10:
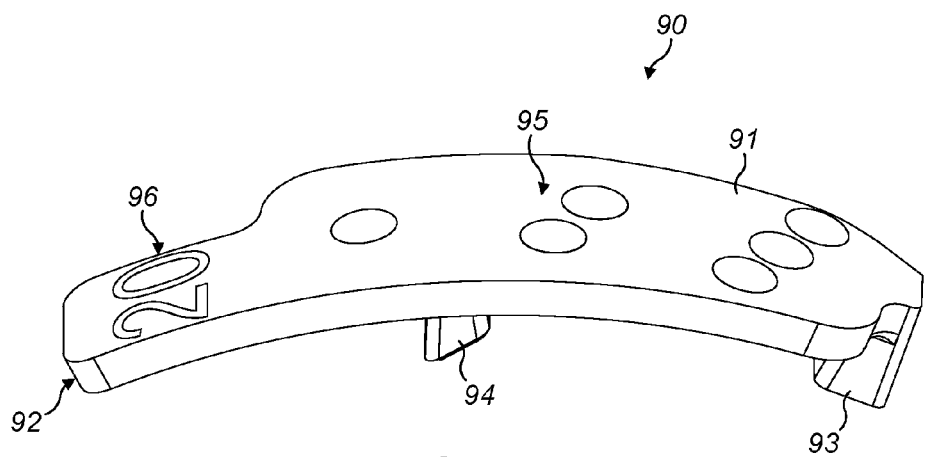
FIG. 10 is a perspective view of a priming indicator according to the present disclosure.

In a first difference, the dose counter of the pMDI 1 is provided with an additional component in the form of a priming indicator 90 which is shown in FIG. 10. The priming indicator 90 comprises a curved body 91 which is relatively elongate having a length which is significantly greater than its width. In addition, the thickness of the curved body 91 is relatively small.

The priming indicator 90 is provided with a pair of legs. A first leg 93 is provided at one end of the curved body 91 (the right-hand end as viewed in FIG. 10) and a second leg 94 is arranged approximately midway along the length of the curved body 91. Each of the first leg 93 and the second leg 94 project from a rear face of the priming indicator 90 and perpendicularly thereto. The first leg 93 is wider than the second leg 94, (the 'width' of the legs being measured in the 'length' direction of the curved body 91).

The front face of the curved body 91 is provided with one or more priming indicia 95 spaced along the length of the curved body 91. In the illustrated example, three priming indicia 95 are provided in the form of three, two and one dots.

Optionally, and as shown in the example of FIG. 10, the end of the curved body 91 distal the first leg 93 (the left-hand end as viewed in FIG. 10) has a reduced width portion 92. A dose indicia 96 (or part of a dose indicia) is provided on the front face of the reduced width portion 92. In the example illustrated, the dose indicia 96 is the numeral '20' which in use will form part of the number '200'.

Figure 11:
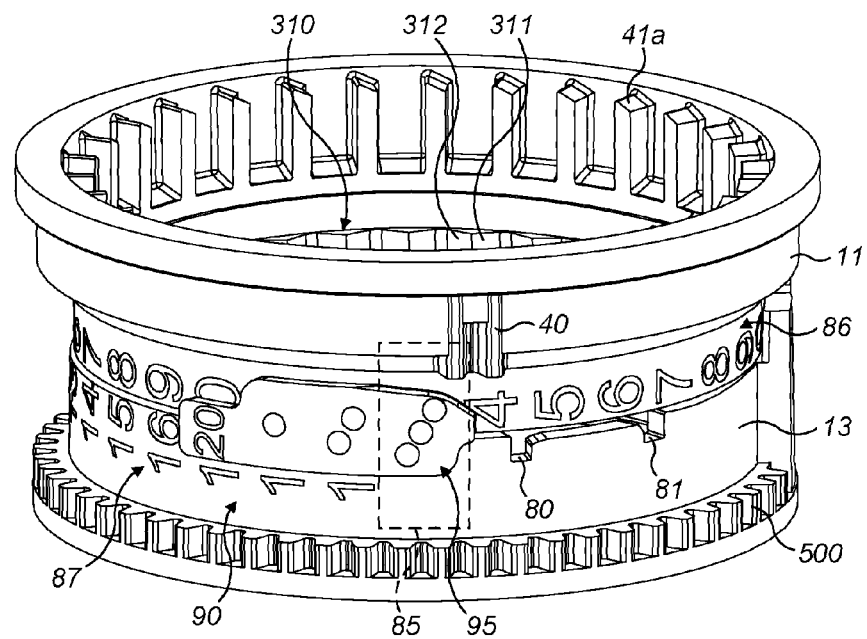
FIG. 11 is a perspective view from a first angle of first and second number rings and the priming indicator of FIG. 10 in an initial position before priming.

In a second difference, the first number ring 11 and the second number ring 13 are provided with notches in their mutually-facing annular edges. For example, as shown in FIG. 11, the second number ring 13 comprises a first notch 81 and a second notch 80. Both the first notch 81 and the second notch 80 have a rectangular cross-section and are both formed in the upper annular edge of the second number ring 13 so that the open mouths of the first and second notches 81, 80 face upwards when viewed in the orientation shown in FIG. 11.

First number ring 11 also comprises a pair of notches which are obscured in FIG. 11. The notches can be seen in FIGS. 13 to 16 and comprise a first notch 88 and a second notch 89. As with the notches of the second number ring 13, the first notch 88 and the second notch 89 are both rectangular in shape but in this instance are provided on the lower annular edge of the first number ring 11 so as to face downwards when viewed in the orientation of FIGS. 12 to 16.

The first and second notches 81, 80 of the second number ring 13 are spaced apart from one another by a set distance. The first and second notches, 88, 89 of the first number ring 11 are also set apart from each other by the same set distance.

The second notch 80 of the second number ring 13 is narrower than the first notch 81 of the second number ring 13. Similarly, the second notch 89 of the first number ring 11 is narrower than the first notch 88 of the first number ring 11. The legs 93, 94 and the notches 80, 81, 88, 89 are configured to form co-operating formations. Importantly, the width of the second notch 80 of the second number ring 13 and the second notch 89 of the first number ring 11 are sized to be able to receive the thinner second leg 94 of the priming indicator 90 but to be too narrow to receive the wider first leg 93 of the priming indicator 90. The first notch 81 of the second number ring 13 and the first notch 88 of the first number ring 11 are configured to be wide enough to receive the first leg 93 of the priming indicator 90.

As noted above, the first and second number rings 11, 13 are provided with dose indicia. In FIGS. 11 to 17, the dose indicia 86 of the first number ring 11 comprise three sequential arrays of numerals '9' to '0'. The dose indicia 87 of the second number ring 13 comprise an array of numerals '19' to '_1' followed by a space bearing no numeral. In addition, as shown in FIG. 13, the second number ring 13 is provided with a red zone marking 87a which extends from the '_2' dose indicia 87 to the space bearing no numeral. The red zone marking 87a provides an additional indication to the user that the pMDI 1 is nearly empty or empty (in the illustrated example the red zone marking 87a will be visible for the last 20 doses of the life of the pMDI 1).

FIG. 11 illustrates an initial position of the dose counter before priming of the pMDI 1 has taken place. For clarity reasons FIG. 11 has omitted other features of the dose counter and pMDI other than the first number ring 11, second number ring 13 and the priming indicator 90. For clarity, the viewing location of the dose counter (the portion of the dose counter visible to the user from outside the pMDI) is illustrated by the dashed rectangle 85. For example, rectangle 85 illustrates the location of the viewing window 30 formed in the lower body 5 of the pMDI 1 as shown in FIGS. 1 and 17.

In the initial position of FIG. 11, the priming indicator 90 is coupled to the first number ring 11 by virtue of the engagement of the first leg 93 in the first notch 88 and the second leg 94 in the second notch 89. As can be seen from FIGS. 13 and 14, the size and shape of the first and second legs 93, 94 are configured to fit in the first notch 88 and second notch 89 respectively. The priming indicator 90 is thus held up in the position shown in FIG. 11 wherein the curved body 91 of the priming indicator 90 partly overlies the outer face of the first number ring 11 and partly overlies the outer face of the second number ring 13. The priming indicator 90 is prevented from dropping downwards in the orientation as viewed in FIG. 11 by virtue of the fact that the first leg 93 and second leg 94 rest on the upper annular edge of the second number ring 13. The priming indicator 90 is prevented from de-coupling from the number rings 11, 13 in the radially outward direction by virtue of the presence of the surrounding housing which is not illustrated in FIGS. 11 to 16.

Figure 17:
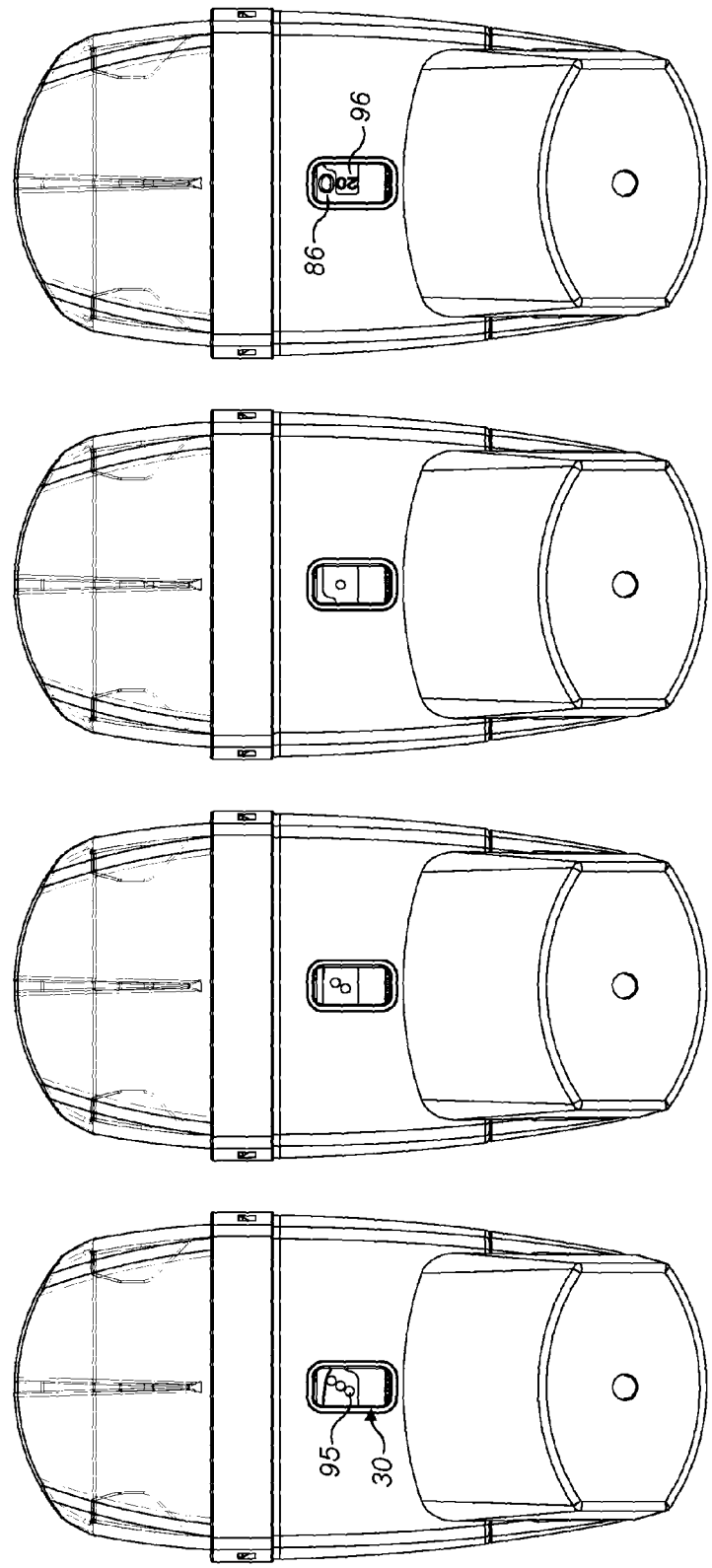
FIG. 17 shows a front view of four configurations of a dispensing apparatus according to the present disclosure.

In the initial position of FIG. 11, the priming indicia 95 showing three dots is located at the viewing location 85 as illustrated in the first illustration of FIG. 17. This is intended to inform the user that three priming actuations are still required before the pMDI 1 is ready for normal use. In this position the priming indicator 90 obscures viewing of the dosage indicia 86 of the first number ring 11. Preferably, and as shown in FIG. 11, the second number ring 13 has a gap in its array of dosage indicia 87 where a '20' indicia would otherwise be positioned.

To prime the pMDI 1, the user carries out a first priming actuation by operating the pMDI 1 in the manner described above and in the referenced application EP 1 859 829. As will be appreciated, this priming actuation causes the first counter ring 11 to rotate by one incremental step. This moves the first counter ring 11 from the position shown in FIGS. 11 and 13 to the position shown in FIG. 14.

Figure 14:
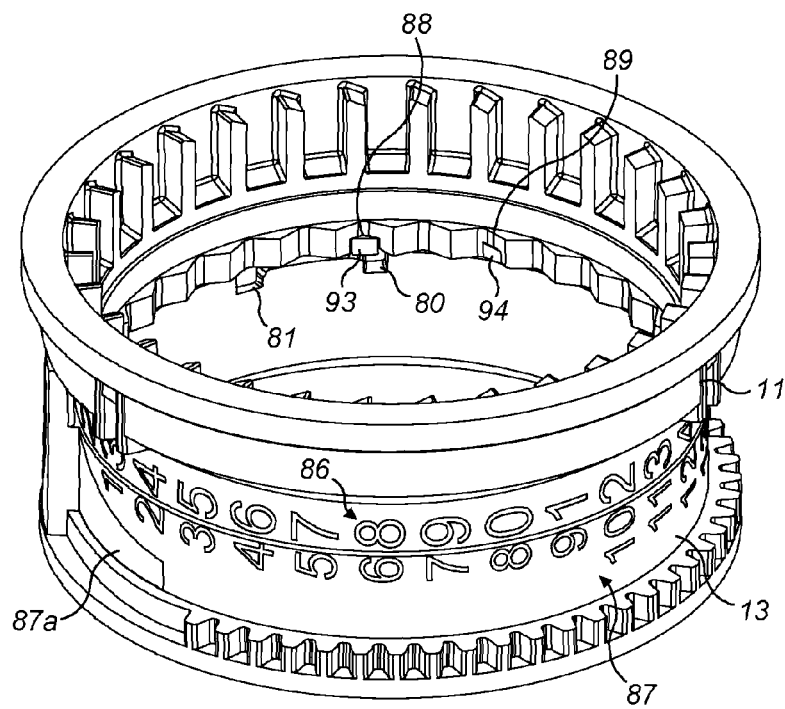
FIG. 14 is a perspective view from the reverse angle showing the arrangement of FIG. 11 after a first priming actuation.

As shown in FIG. 14, after completion of the first priming actuation, the first number ring 11 has rotated to the point where the first notch 88 containing the first leg 93 of the priming indicator 90 has just passed the location of the second notch 80 of the second number ring 13. Due to the fact that the first leg 93 is wider than the second notch 80, the first leg 93 does not drop into the second notch 80 but rides over the second notch 80 and the priming indicator 90 remains coupled to the first number ring 11. At this point the priming indicia 95 showing two dots is now aligned with the viewing location 85 as illustrated in the second illustration of FIG. 17.

Figure 15:
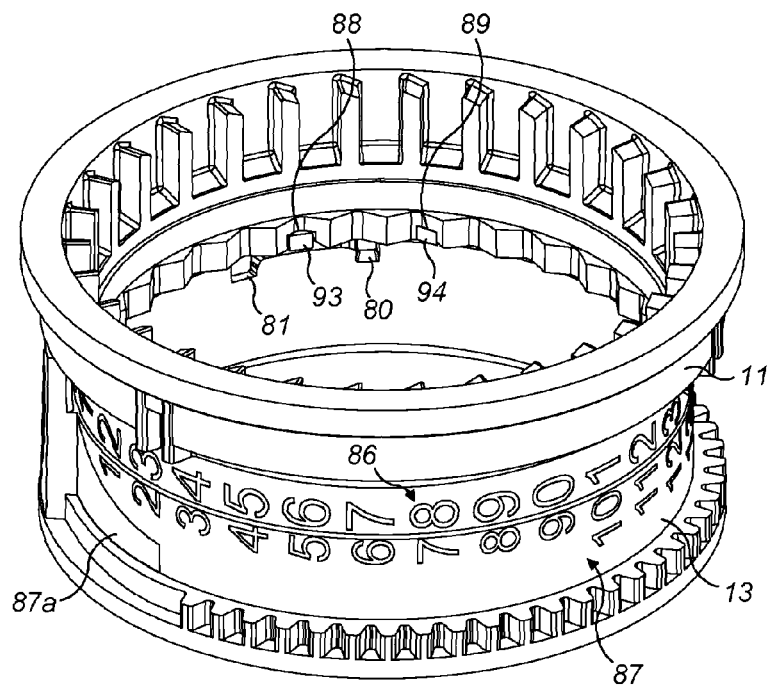
FIG. 15 is a perspective view from the reverse angle showing the arrangement of FIG. 11 after two priming actuations.

Next, a second priming actuation is carried out which moves the dose counter into the configuration shown in FIG. 15. As can be seen, the first leg 93 and second leg 94 of the priming indicator 90 have continued to ride along the upper annular edge of the second number ring 13. At this point, the priming indicia 95 showing a single dot is aligned with the viewing location 85 as illustrated in the third illustration of FIG. 17.

Figure 12:
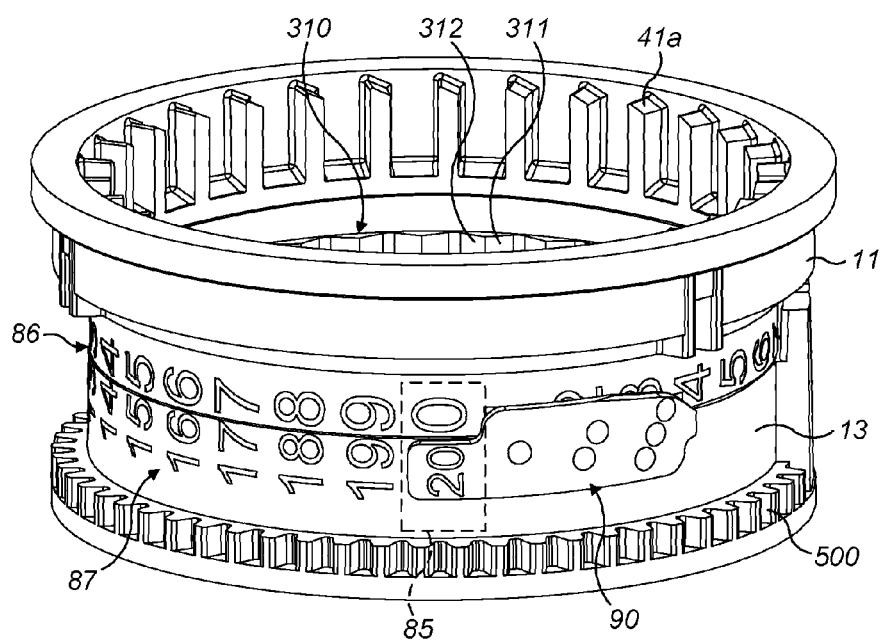
FIG. 12 is a perspective view of the first and second number rings and the priming indicator of FIG. 11 in a second position immediately after priming.
Figure 13:
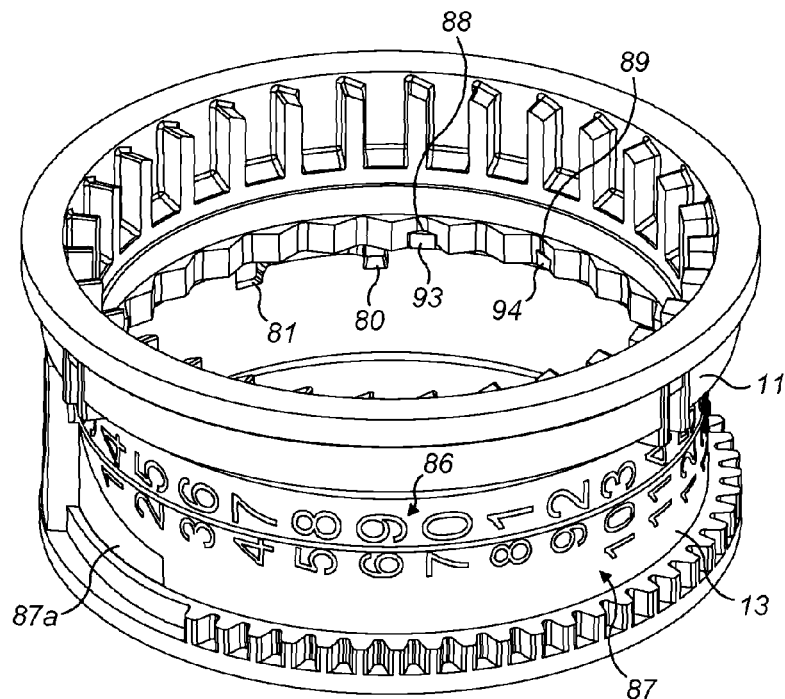
FIG. 13 is a perspective view showing the arrangement of FIG. 11 (before priming) from a reverse angle.
Figure 16:
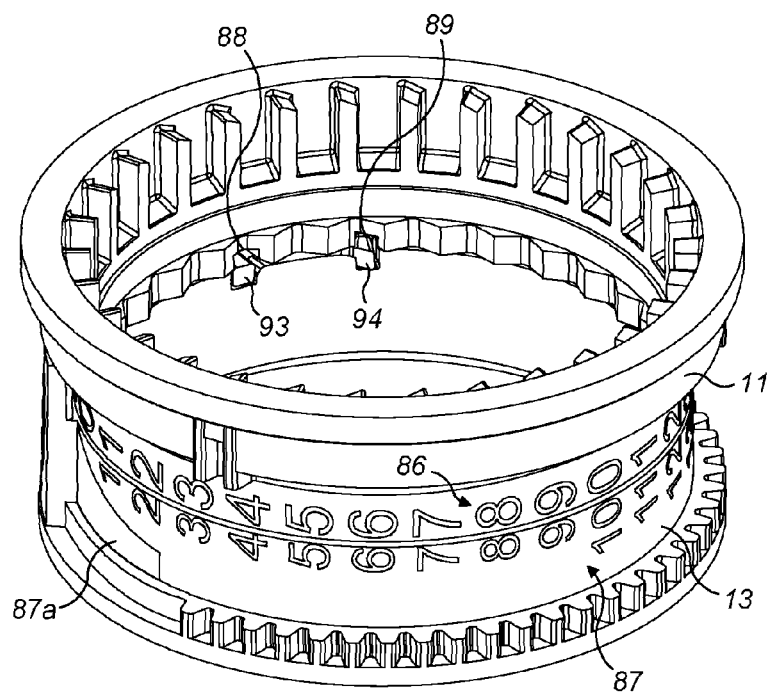
FIG. 16 is a perspective view showing the arrangement of FIG. 12 (after three priming actuations) from the reverse angle.

Next, a third and final priming actuation is carried out which moves the dose counter into the configuration shown in FIGS. 12 and 16. As can be seen best in FIG. 16, the first number ring 11 has now been rotated to the point where the notches 81, 80 of the second number ring 13 have become aligned with the notches 88, 89 of the first number ring 11. This allows the first leg 93 and the second leg 94 of the priming indicator 90 to drop down into the first notch 81 and the second notch 80 respectively of the second number ring 13. Thus, the priming indicator 90 drops under gravity to de-couple from the first number ring 11 and to become coupled to the second number ring 13. The consequence of this for the user is shown in FIG. 12 and in the fourth illustration of FIG. 17 where it can be seen that the first number ring 11 is no longer obscured by the priming indicator 90 as the priming indicator 90 has moved to a point where it no longer overlies the first number ring 11. In the illustrated example, the priming indicator 90 still overlies the array of dose indicia 87 of the second number ring 13 within the viewing location 85 but is aligned such that the dose indicia 96 in the form of the numerals '20' on the priming indicator 90 is displayed instead. This together with the '0' numeral of the dose indicia 86 of the first number ring 11 displays the correct, first, dose indicia '200' of the dose counter. This conveys the information to the user that the pMDI 1 has been primed and is now ready for normal use. Of course, it will be appreciated that the priming indicator 90 could be adapted by removing the reduced width portion 92 such that after the third priming actuation no part of the priming indicator 90 is visible at the viewing location 85.

It will be noted that during the subsequent normal actuations of the pMDI 1, the first number ring 11 will continue to rotate as before and after every 10 actuations will incrementally rotate the second number ring 13. The priming indicator 90 will remain coupled to the second number ring 13 and move in sync with it for the rest of the life of the pMDI 1. However, the configuration of the dose counter is that the second number ring 13 does not complete a single full revolution during the normal life of the pMDI 1. Thus, the priming indicator 90 never moves back into sight at the viewing location 85. Consequently, once the priming indicator 90 has carried out its function at the start of life of the pMDI 1 to prompt a user it to carry out the required number of priming actuations it no longer stays visible and therefore does not inhibit in any way the correct reading of the dose counter during normal use.

The invention claimed is:
1. A dose counter for displaying a count indication of the number or quantity of doses dispensed from or remaining in a container associated, in use, with the dose counter, the dose counter comprising:
- an indicator member comprising dose indicia; and
- a priming indicator for prompting a user to carry out one or more priming actuations of the container;
- wherein the priming indicator is initially arranged to at least partially overlie the indicator member to thereby at least partially obscure viewing of the dose indicia of the indicator member until the one or more priming actuations of the container have been completed;
- wherein the priming indicator is movable after the one or more priming actuations have been completed into a disposition where it no longer obscures viewing of the dose indicia of the indicator member.

2. The dose counter of claim 1 wherein the priming indicator is movable into the disposition where it no longer obscures viewing of the dose indicia of the indicator member by movement of the indicator member itself.

3. The dose counter of claim 1 wherein the priming indicator is a separate component from the indicator member.

4. The dose counter of claim 1 wherein the priming indicator comprises priming indicia.

5. The dose counter of claim 4 wherein the priming indicia comprise one or more indicia selected from the group of: dots; numbers; colours; and pictograms.

6. The dose counter of claim 4 wherein a different style of indicia is used to form the priming indicia compared to the dose indicia.

7. The dose counter of claim 1 wherein the priming indicator is movable after the one or more priming actuations have been completed into a disposition where it no longer overlies the indicator member.

8. Dispensing apparatus comprising a dose counter as claimed in claim 1.

9. Dispensing apparatus as claimed in claim 8 further comprising a container containing a quantity of substance to be dispensed.

10. Dispensing apparatus as claimed in claim 8 comprising a viewing window for viewing the count indication of the dose counter, wherein the priming indicator is initially arranged at least partially inbetween the indicator member and the viewing window to thereby at least partially obscure viewing of the dose indicia of the indicator member until the one or more priming actuations of the container have been completed;
- wherein the priming indicator is movable after the one or more priming actuations have been completed into a disposition where it is no longer inbetween the viewing window and the indicator member.

11. Dispensing apparatus as claimed in claim 8 being a pressurised metered dose inhaler or a pump.

12. The dose counter of claim 1 wherein the priming indicator is initially coupled to the indicator member to thereby be moved with the indicator member during the one or more priming actuations.

13. The dose counter of claim 12 wherein the priming indicator is able to be decoupled from the indicator member after the one or more priming actuations have been completed.

14. The dose counter of claim 13 wherein the priming indicator is able to be decoupled from the indicator member by the action of gravity.

15. The dose counter of claim 1 wherein the indicator member comprises a rotatable member.

16. The dose counter of claim 15 wherein the indicator member comprises an annular ring wherein the dose indicia are arranged on an outer peripheral face of the annular ring.

17. The dose counter of claim 1 wherein the indicator member and the priming indicator comprise co-operating formations for coupling the priming indicator to the indicator member.

18. The dose counter of claim 17 wherein the co-operating formations comprise one or more legs provided on the priming indicator and one or more apertures in the indicator member.

19. The dose counter of claim 18 wherein the one or more apertures comprise one or more notches or indentations in an edge of the indicator member.

20. The dose counter of claim 1 wherein the indicator member forms a first indicator member of the dose counter and the dose counter further comprises a second indicator member, the first and second indicator members acting in combination to display the count indication.

21. The dose counter of claim 20 wherein the first indicator member is arranged to move on each actuation of the associated container and the second indicator member is arranged to move after a predetermined number of incremental movements of the first indicator member.

22. The dose counter of claim 20 wherein the dose indicia of the first indicator member displays a 'units' numeral of the count indication and wherein the second indicator member comprises dose indicia which display a 'tens' numeral.

23. The dose counter of claim 22 wherein the dose indicia of the first indicator member comprises a plurality of sequentially arranged arrays of 'units' numerals, each array ranging from '9' to '0'.

24. The dose counter of claim 20 wherein the priming indicator is initially arranged to at least partially overlie the first indicator member and to at least partially overlie the second indicator member to thereby at least partially obscure viewing of the dose indicia of both the first and second indicator members.

25. The dose counter of claim 20 wherein the priming indicator is initially coupled to the first indicator member to thereby be carried with the first indicator member and to be moved relative to the second indicator member during the one or more priming actuations.

26. The dose counter of claim 25 wherein the priming indicator is arranged to be decoupled from the first indicator member after the one or more priming actuations have been completed.

27. The dose counter of claim 26 wherein the priming indicator is arranged to become coupled with the second indicator member on decoupling from the first indicator member.

28. The dose counter of claim 27 wherein after coupling of the priming indicator to the second indicator member, the priming indicator is carried with the second indicator member during subsequent actuations of the associated container.

29. The dose counter of claim 25 wherein the first indicator member, the second indicator member and the priming indicator comprise co-operating formations for coupling the priming indicator initially to the first indicator member and subsequently to the second indicator member.

30. The dose counter of claim 29 wherein the co-operating formations comprise one or more legs provided on the priming indicator and one or more apertures in the first and second indicator members.

31. The dose counter of claim 30 wherein the one or more apertures comprise one or more notches or indentations in an edge of the first and/or second indicator members.

32. The dose counter of claim 20 wherein the first indicator member and the second indicator member both comprise a rotatable member.

33. The dose counter of claim 32 wherein both the first indicator member and the second indicator member each comprise an annular ring having dose indicia arranged on an outer peripheral face of the annular ring.

34. The dose counter of claim 20 wherein the dose indicia of the first indicator member displays a 'units' numeral of the count indication and wherein the second indicator member comprises dose indicia which display a 'tens' numeral and additionally a 'hundreds' numeral of the count indication.

35. The dose counter of claim 20 wherein the priming indicator is movable after the one or more priming actuations have been completed into a disposition where it no longer overlies the first indicator member.

\* \* \* \* \*